United States Patent [19]
Luce

[11] Patent Number: 4,585,996
[45] Date of Patent: Apr. 29, 1986

[54] INSTRUMENT FOR MEASURING ELECTRICAL CONDUCTIVITY OF A LIQUID

[75] Inventor: Robert S. Luce, Los Altos, Calif.

[73] Assignee: Lockheed Missiles & Space Company, Inc., Sunnyvale, Calif.

[21] Appl. No.: 498,978

[22] Filed: May 27, 1983

[51] Int. Cl.$^4$ ........................................... G01N 27/02
[52] U.S. Cl. ................................. 324/442; 324/57 SS
[58] Field of Search ............... 324/439, 441, 442, 445, 324/449, 57 PS, 57 SS, DIG. 1, 3, 300; 323/302; 204/400, DIG. 9

[56] References Cited

U.S. PATENT DOCUMENTS

| | | | |
|---|---|---|---|
| 3,281,681 | 4/1962 | Stevenson | 324/439 |
| 3,296,523 | 1/1967 | Haas | 324/57 SS |
| 3,493,857 | 2/1970 | Silverman | 324/442 |
| 3,906,353 | 9/1975 | Murdock | 324/442 |
| 4,011,504 | 3/1977 | DePillo | 324/115 |
| 4,042,482 | 8/1977 | Shannon | 204/242 |
| 4,066,948 | 1/1978 | Hawk | 324/442 |
| 4,303,887 | 12/1981 | Hill | 324/441 |

OTHER PUBLICATIONS

Electronic Measurements, by Terman and Pettit, McGraw-Hill Co., 1952, p. 574.

Primary Examiner—Michael J. Tokar
Attorney, Agent, or Firm—John J. Morrissey

[57] ABSTRACT

An instrument for measuring electrical conductivity of a liquid comprises a two-electrode probe for insertion into the liquid. A triangular waveform generator (IC4 and IC5) impresses a voltage of fixed amplitude on one electrode of the probe by means of driver circuitry (IC3). This voltage drives an electric current through the liquid to the other electrode of the probe. Receiver circuitry (IC6) detects the current at this other electrode, and converts the detected current to a triangular wavefore AC voltage signal. Amplifier circuitry (IC1) amplifies the output of the receiver circuitry, and the amplified voltage signal is converted to a smoothed DC voltage signal by precision rectifier circuitry (IC2 and IC7). The output of the precision rectifier circuitry is processed to obtain a signal indicative of electrical conductivity of the liquid.

5 Claims, 3 Drawing Figures

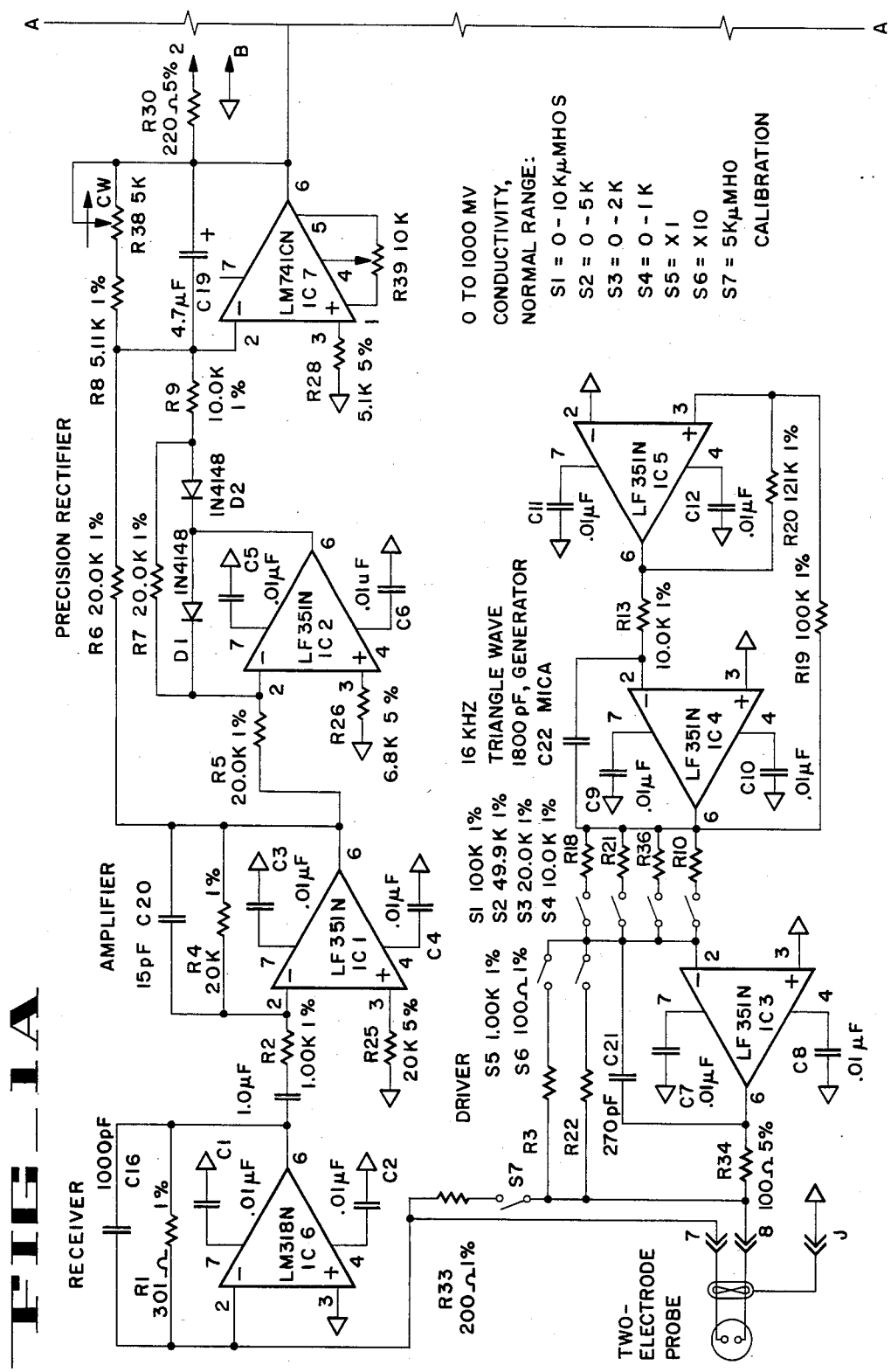

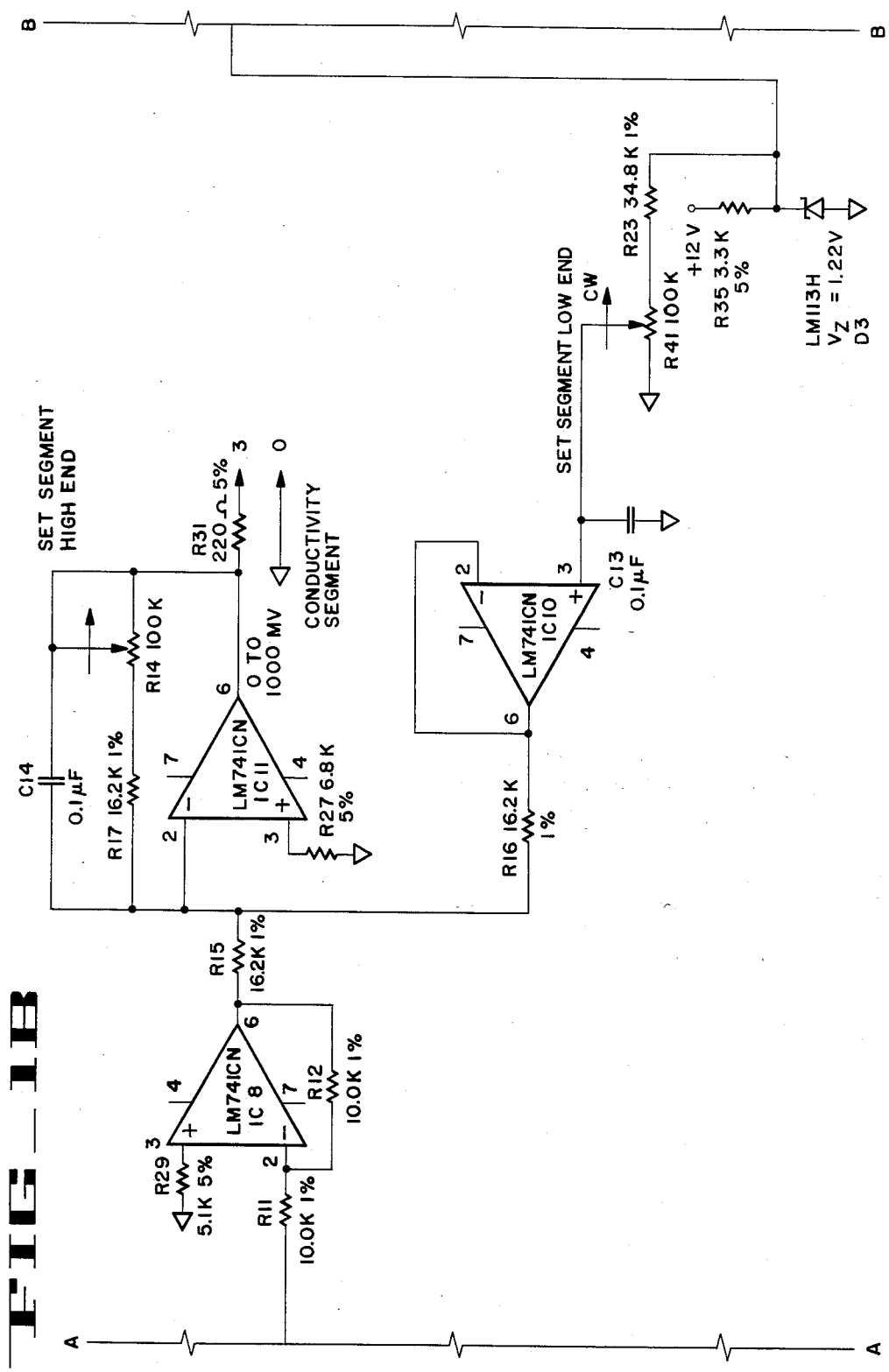
FIG_1B

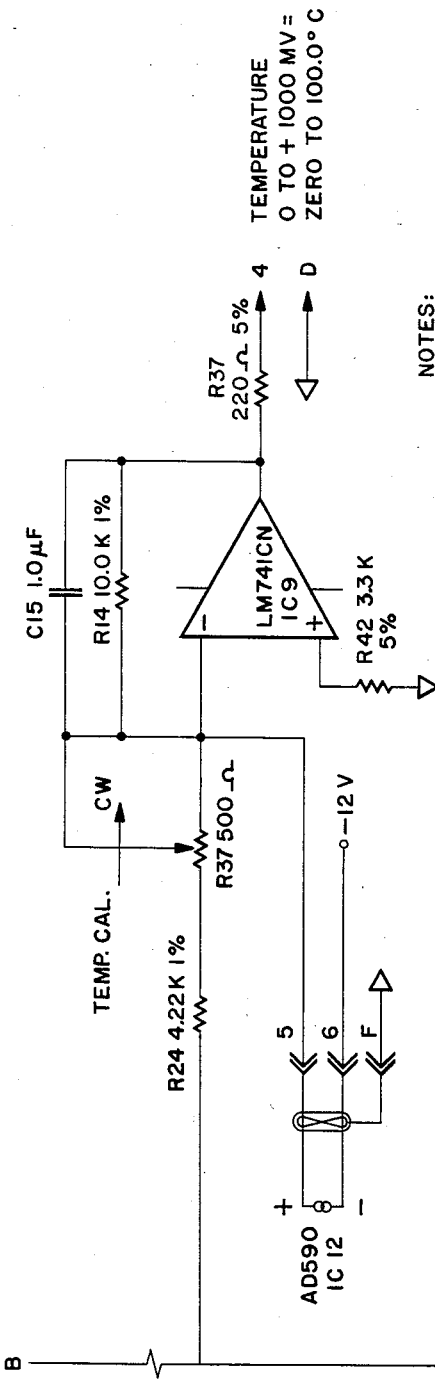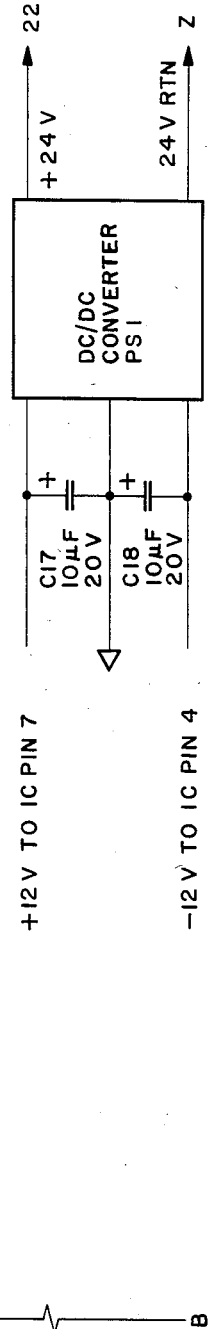

INSTRUMENT FOR MEASURING ELECTRICAL CONDUCTIVITY OF A LIQUID

TECHNICAL FIELD

This invention relates to apparatus for measuring electrical conductivity of liquids.

DESCRIPTION OF THE PRIOR ART

Electrical conductivity of a liquid is conventionally determined by inserting a first electrode and a second electrode into the liquid, impressing a voltage signal of sufficient amplitude on the first electrode to drive a current through the liquid to the second electrode, and detecting the current at the second electrode. The current detected at the second electrode is converted to a voltage signal, which is then amplified, rectified, smoothed, and scaled to produce a measurement expressed in micromhos indicating the reciprocal of the electrical resistance (i.e., the transconductance or "conductivity") of the liquid.

With two-electrode instruments used in the prior art to measure electrical conductivity of a liquid, the voltage signal impressed on the first electrode typically had a square waveform or a sinusoidal waveform. Consequently, in using an instrument of the prior art to measure electrical conductivity of a liquid, the relationship between the output signal indicating the conductivity of the liquid and the input voltage signal impressed upon the first electrode of the instrument was strictly linear only in the low to middle conductivity range of the instrument.

With instruments of the prior art for measuring electrical conductivity of a liquid, there was no practicable way to generate segmental output signals corresponding to selected segments of the amplitude range of the input voltage signal, where each segmental output signal could be precisely correlated with the full-scale output signal.

SUMMARY OF THE INVENTION

It is an object of the present invention to provide a two-electrode instrument for measuring electrical conductivity of a liquid, where the relationship between an input voltage signal impressed upon one electrode and an output conductivity signal derived from current detected at the other electrode is linear over substantially the entire amplitude range of the input voltage signal.

It is a particular object of the present invention to provide an apparatus comprising a two-electrode probe whereby electrical conductivity of a liquid can be measured by impressing a voltage signal of triangular waveform on the first electrode of the probe, and by processing a resulting current signal detected at the second electrode of the probe.

It is a further object of the present invention to provide an apparatus for measuring electrical conductivity of a liquid by applying a voltage signal to a first electrode and detecting a signal at a second electrode indicative of current passing through the liquid between the first and second electrodes, and by processing the current signal at the second electrode to obtain selectively either a full-scale output signal indicative of conductivity over the full amplitude range of the input voltage signal, or a segmental output signal indicative of conductivity over a corresponding segmental portion of the input signal range.

It is likewise an object of the present invention to provide an apparatus for measuring electrical conductivity of a liquid, and for independently measuring temperature of the liquid and generating a temperature signal to correct the conductivity measurement for variations attributable to the particular chemical composition of the liquid.

A conductivity-measuring instrument in accordance with the present invention comprises a first electrode and a second electrode insertable into a liquid whose electrical conductivity is to be measured, electronic circuitry for impressing an input voltage signal of triangular waveform on the first electrode so as to drive an alternating electrical current through the liquid to the second electrode, and electronic circuitry for detecting the current at the second electrode and for converting the detected current into an input voltage signal that is processed to produce a signal expressed in michromhos representing the electrical conductivity of the liquid. The instrument further comprises segment-expanding electronic circuitry for selectively amplifying particular ranges of the full-scale conductivity signal.

A conductivity-measuring instrument in accordance with the present invention also comprises temperature sensing circuitry to provide a temperature signal that is independent of the electrical conductivity of the liquid. This feature is important because the correlation between temperature and electrical conductivity varies according to the constituents of the liquid. It is possible with an independently generated temperature signal to compensate the conductivity signal for any variation attributable to the chemical composition of the particular liquid.

DESCRIPTION OF THE DRAWING

FIG. 1, which comprises FIGS. 1A, 1B and 1C, is a schematic diagram of electronic circuitry (preferably formed on a printed circuit card) for a conductivity-measuring instrument in accordance with the present invention.

BEST MODE OF CARRYING OUT THE INVENTION

A conductivity-measuring instrument according to the preferred embodiment of the present invention comprises a two-electrode probe for insertion into a liquid whose electrical conductivity is to be measured and/or monitored. In operation, each electrode is immersed in the liquid with a gap between the two electrodes. A schematic representation of the probe is labelled in the lower left-hand portion of FIG. 1A. Probes of this type are commercially available, e.g., the probe marketed by Cole-Parmer Instrument Company under catalog No. D1485-40.

The probe as shown in FIG. 1A comprises a first electrode on which a voltage is impressed to drive an electric current through the liquid, and a second electrode to which the current is driven. The electrical conductivity of the liquid is measured in micromhos, which is mathematically the reciprocal of the electrical resistance of the liquid measured in microohms. Electrical leads to the first and second electrodes of the probe comprise a twisted pair of shielded conducting wires, the shield of which is grounded as indicated by attachment to grounded terminal J of a printed circuit card on which electronic circuitry for the instrument is formed.

A 16-kilohertz triangular waveform generator (so labelled in FIG. 1A) generates an input voltage signal of fixed amplitude, which is impressed on the first electrode of the two-electrode probe by means of driver circuitry (so labelled in FIG. 1A). The triangular waveform generator is of conventional design, and comprises operational amplifiers IC4 and IC5 connected together in a closed loop. The amplifier IC4 functions as an integrating amplifier for generating triangular waveform ramps. The amplifier IC5 functions as a level detector, and serves as the input voltage source for the first electrode of the probe and as a reset subcircuit component for the integrating amplifier IC4. Power to the triangular waveform generator is provided by an external power supply connected to pins 7 and 4 of the amplifiers IC4 and IC5 as indicated in FIG. 1A. A preferred power supply is schematically illustrated in the lower right-hand portion of FIG. 1C.

The driver circuitry comprises an operational amplifier IC3, which is configured as a selectable-gain inverting amplifier by means of switch-selectable feedback resistors R3 and R22, and input resistors R18, R21, R36 and R10. The driver circuitry enables the conductivity range of the instrument to be set according to the anticipated or desired conductivity characteristics of a particular liquid whose electrical conductivity is being monitored.

Receiver circuitry (so labelled in FIG. 1A) detects the current conducted through the liquid from the first electrode to the second electrode, and converts the current so detected into an appropriately scaled voltage signal. The receiver circuitry is of conventional design, and comprises an operational amplifier IC6 with an amplifier feedback loop that includes a current-to-voltage scaling resistor R1 whereby the amplifier IC6 is configured as a current-to-voltage converter. The output of the receiver circuitry has a low-level triangular waveform AC voltage.

The triangular waveform AC voltage output from the receiver circuitry is increased in amplitude by amplifier circuitry (so labelled in FIG. 1A). The amplifier circuitry is of conventional design, and comprises an operational amplifier IC1 configured as an inverting voltage amplifier by means of feedback resistor R4 and input resistor R2.

The amplified triangular waveform AC voltage signal is converted to a smoothed DC voltage signal by means of precision rectifier circuitry (so labelled in FIG. 1A). The precision rectifier circuitry is of conventional design, and comprises operational amplifiers IC2 and IC7 configured by means of appropriate resistors, diodes and capacitors for rectifying and smoothing the amplified triangular voltage waveform. The variable resistor R39 enables the zero reading (i.e, the zero conductance level) of the instrument to be adjusted when the first and second electrodes are removed from the conductive liquid. The variable resistor R38 enables the scale factor of the selected conductivity range to be adjusted when a resistance of known value is placed across the first and second electrodes for calibration purposes. The output of the precision rectifier circuitry is a positive-going voltage that is scaled proportionately to the conductivity of the liquid being measured.

The output of the precision rectifier circuitry is a positive DC voltage having a value in the from 0 volts to an arbitrarily specified upper limit of +1000 millivolts, which corresponds to a conductivity range extending from 0 micromhos to a selected upper limit, e.g., 5000 micromhos. This output is available at pin 2 relative to terminal B on the printed circuit card, and is applied to pin 2 of an amplifier IC8 shown on FIG. 1B. The amplifier IC8 is configured as a unity-gain inverting amplifier by means of resistors R11 and R12, and serves to invert the output of the precision rectifier circuitry so as to produce a negative DC voltage.

A second output of the precision rectifier circuitry is made available at pin 3 relative to terminal 0 on the printed circuit card. This second output is obtained from an amplifier IC11, which is configured as an adding and scaling amplifier by means of input resistors R15 and R16 and feedback resistors R17 and R14. This second output is a positive DC voltage likewise having a value in the range from 0 volts to +1000 millivolts. However, this +1000 millivolt range of the second output of the precision rectifier circuitry corresponds to a particular segment (e.g., the segment from 2500 micromhos to 3500 micromhos) of the conductivity range. In effect, this second output of the precision rectifier circuitry represents an expansion of a segment of particular interest in the conductivity range of the instrument.

The full-scale negative DC voltage output of the amplifier IC8 is algebraically added to a positive voltage signal provided by a precision voltage reference diode D3 (seen in the lower right-hand portion of FIG. 1B) as scaled by resistors R23 and R41 and buffered by amplifier IC10, which is configured as a unity-gain, noninverting, low-output-impedance amplifier. The effect of this algebraic addition is to weight the zero-voltage output of the amplifier IC8 so as to represent a selected value of conductance other than 0 micromhos (e.g., 2500 micromhos), which is the lower end of the particular segment of interest in the conductivity range of the instrument. Adjustment of the variable resistor R41 enables selection of a particular micromho value of conductance for representation by a 0-volt output from the amplifier IC11. The upper end of the expanded conductivity scale segment is determined by adjustment of the variable resistor R14, which determines the gain of the amplifier IC11.

In operation, adjustment of the resistor R41 enables the value of the lower end of the expanded conductivity scale (e.g., 2500 micromhos) to be set, and adjustment of the resistor R14 enables the value of the upper end of the expanded conductivity scale (e.g., 3500 micrombos) to be set. These adjustments can be accomplished by using conductive liquids of known electrical conductivity, or by placing resistances of known values across the first and second electrodes, for calibration purposes. The circuit as shown in FIGS. 1A and 1B permits expansion of any segment of interest of the conductivity scale to approximately six times the normal (i.e., the unexpanded) range.

A separate temperature measuring circuit, as shown in FIG. 1C, is included on the printed circuit card. Temperature measurement is accomplished with a two-terminal integrated-circuit temperature transducer IC12 operating in conjunction with an operational amplifier IC9. The temperature transducer is preferably of the type marketed by Analog Devices under catalog No. AD590. The operational amplifier IC9 is configured as specified by the manufacturer of the temperature transducer. The temperature measuring circuit shown in FIG. 1C produces a 0-volt to +1000-millivolt signal corresponding to a 0° C. to 100.0° C. temperature range.

A particular embodiment of an instrument in accordance with the present invention for measuring electrical conductivity of a liquid has been described herein. However, other embodiments suitable for particular applications would become apparent to workers skilled in the art upon perusal of the foregoing specification and accompanying drawing. Thus, the description presented herein is to be understood as illustrative of the invention, which is more generally defined by the following claims and their equivalents.

I claim:

1. An instrument for measuring electrical conductivity of a liquid, said instrument comprising:
   (a) a first electrode and a second electrode, each of said first and second electrodes being immersible in said liquid;
   (b) means for impressing an input voltage signal having a triangular waveform on said first electrode, said triangular waveform having a substantially constant rate of voltage change through periodic changes in polarity of said input voltage signal, said input voltage signal integrating substantially to zero over each cycle of said triangular waveform, said input voltage signal having sufficient amplitude to drive an alternating electrical current through said liquid to said second electrode when said first and second electrodes are immersed in said liquid;
   (c) means for detecting said alternating electrical current at said second electrode, and for converting said current detected at said second electrode to an output voltage signal; and
   (d) means for processing said output voltage signal to obtain a signal indicative of electrical conductivity of said liquid.

2. The instrument of claim 1 wherein said means for processing said output voltage signal comprises means for amplifying and rectifying said output voltage signal to obtain a full-scale conductivity signal indicative of electrical conductivity of said liquid, said full-scale conductivity signal being provided on a full-scale range of said instrument.

3. The instrument of claim 2 further comprising means for expanding a segment of said full-scale range of said instrument, said segment of said full-scale range corresponding to a particular voltage range of said input voltage signal impressed on said first electrode.

4. The instrument of claim 1 further comprising means for measuring temperature of said liquid, and means for generating a temperature-indicative signal that is independent of electrical conductivity of said liquid.

5. The instrument of claim 4 wherein said means for generating said temperature-indicative signal comprises a two-terminal integrated-circuit temperature transducer operating in conjunction with an operational amplifier.

* * * * *